US012576288B2

(12) United States Patent
Li

(10) Patent No.: US 12,576,288 B2
(45) Date of Patent: Mar. 17, 2026

(54) RADIOTHERAPY SYSTEM

(71) Applicant: OUR UNITED CORPORATION, Xi'an (CN)

(72) Inventor: Jinsheng Li, Xi'an (CN)

(73) Assignee: OUR UNITED CORPORATION, Xi'an (CN)

(*) Notice: Subject to any disclaimer, the term of this patent is extended or adjusted under 35 U.S.C. 154(b) by 238 days.

(21) Appl. No.: 18/446,852

(22) Filed: Aug. 9, 2023

(65) Prior Publication Data

US 2023/0381543 A1 Nov. 30, 2023

Related U.S. Application Data

(63) Continuation-in-part of application No. PCT/CN2021/076388, filed on Feb. 9, 2021, and a continuation-in-part of application No. PCT/CN2021/076394, filed on Feb. 9, 2021.

(51) Int. Cl.
*A61N 5/10* (2006.01)

(52) U.S. Cl.
CPC ......... *A61N 5/1081* (2013.01); *A61N 5/1045* (2013.01); *A61N 5/1071* (2013.01)

(58) Field of Classification Search
None
See application file for complete search history.

(56) References Cited

U.S. PATENT DOCUMENTS

2004/0184578 A1* 9/2004 Nakano .................. A61N 5/103
378/65
2006/0163495 A1 7/2006 Hiramoto et al.

2009/0041200 A1 2/2009 Lu et al.
2012/0256103 A1* 10/2012 Luzzara ................. G21K 1/046
250/492.1
2014/0239204 A1 8/2014 Orton et al.
(Continued)

FOREIGN PATENT DOCUMENTS

CN 102105194 A 6/2011
CN 107469240 A 12/2017
(Continued)

OTHER PUBLICATIONS

International Search Report of the International Searching Authority for State Intellectual Property Office of the People's Republic of China in PCT application No. PCT/CN2021/076388 issued on Nov. 1, 2021, which is an international application to which this application claims priority.
(Continued)

*Primary Examiner* — Marcus H Taningco
(74) *Attorney, Agent, or Firm* — Kolitch Romano Dascenzo Gates LLP

(57) ABSTRACT

The present disclosure provides a radiotherapy system, including a treatment couch, a gantry, a treatment head coupled to the gantry, and a control mechanism. The control mechanism is configured to control the gantry to rotate, and synchronously control the treatment couch to move along an axial direction of the gantry; and the treatment head includes a multi-leaf collimator, the multi-leaf collimator being configured so that leaves are capable of stopping at any position along a movement path to form radiation fields of various shapes.

19 Claims, 8 Drawing Sheets

(56) References Cited

U.S. PATENT DOCUMENTS

| | | | |
|---|---|---|---|
| 2014/0263990 A1* | 9/2014 | Kawrykow | A61N 5/1031 |
| | | | 250/252.1 |
| 2015/0094517 A1 | 4/2015 | Prieels | |
| 2016/0325117 A1* | 11/2016 | Arai | G21K 1/046 |
| 2020/0054895 A1* | 2/2020 | Ranganathan | G16H 20/40 |
| 2020/0230437 A1 | 7/2020 | Li | |
| 2021/0031053 A1 | 2/2021 | Zhao et al. | |
| 2021/0304866 A1* | 9/2021 | Kuusela | A61N 5/1039 |
| 2021/0316158 A1* | 10/2021 | Shaw | A61N 5/1081 |

FOREIGN PATENT DOCUMENTS

| | | | |
|---|---|---|---|
| CN | 108379748 A | 8/2018 | |
| CN | 108969909 A | 12/2018 | |
| CN | 109966663 A | 7/2019 | |
| CN | 110732095 A | 1/2020 | |
| CN | 210131259 U | 3/2020 | |

OTHER PUBLICATIONS

International Search Report of the International Searching Authority for State Intellectual Property Office of the People's Republic of China in PCT application No. PCT/CN2021/076394 issued on Sep. 29, 2021, which is an international application to which this application claims priority.

* cited by examiner

RADIOTHERAPY SYSTEM

CROSS-REFERENCE TO RELATED APPLICATIONS

This application is a continuation in part application of international application No. PCT/CN2021/076394, filed on Feb. 9, 2021, and continuation in part application of international application No. PCT/CN2021/076388, filed on Feb. 9, 2021, the disclosures of which are herein incorporated by reference in their entireties.

TECHNICAL FIELD

The present disclosure relates to the field of medical devices, in particular to a radiotherapy system.

BACKGROUND OF THE INVENTION

The radiotherapy system is a medical device that uses radiation beams to treat tumors. The radiotherapy system includes a gantry, a treatment head, and a treatment couch, wherein the treatment couch is configured to carry a patient and move the patient to a designated position, the treatment head is disposed on the gantry and driven by the gantry to rotate around an isocentric axis, and the treatment head focuses a plurality of radiation beams on a gross tumor volume of the patient during rotating, so as to achieve radiotherapy of tumor tissues.

SUMMARY OF THE INVENTION

The present disclosure provides a radiotherapy system.
Specifically, the following technical solutions are provided.
The radiotherapy system includes: a treatment couch, a gantry, a treatment head coupled to the gantry, and a control mechanism; wherein
the control mechanism is configured to control the gantry to rotate, and synchronously control the treatment couch to move along an axial direction of the gantry; and
the treatment head includes a multi-leaf collimator, the multi-leaf collimator being configured so that leaves are capable of stopping at any position along a movement path to form radiation fields of various shapes.

In some embodiments, the treatment head includes a radiation source, a precollimator, and the multi-leaf collimator, wherein the multi-leaf collimator includes a first leaf bank and a second leaf bank which are oppositely disposed, leaves of both leaf banks being moveable along a direction parallel to an axis of the gantry.

In some embodiments, the control mechanism is configured to control a rotating speed of the gantry, a speed of the treatment couch, a position of a leaf in the multi-leaf collimator, or a dose rate of the radiation source, so as to perform intensity modulation on a target volume.

In some embodiments, the control mechanism is configured to control the gantry to rotate, the treatment couch to move along the axial direction of the gantry and the leaves of the multi-leaf collimator to move during an emitting process of a radiation beam by the radiation source.

In some embodiments, the control mechanism is configured to control the gantry to rotate to a specific angle, control the treatment couch to move, along the axial direction of the gantry, to a specific position, control the leaves of the multi-leaf collimator to conform to a radiation field with a specific shape, and control the radiation source to emit a radiation beam.

The present disclosure discloses a radiotherapy system, which includes a treatment couch, a gantry, a treatment head coupled to the gantry, and a control mechanism; wherein the control mechanism is configured to control the gantry to rotate, and synchronously control the treatment couch to move along an axial direction of the gantry; and the treatment head includes a multi-leaf collimator, the multi-leaf collimator being configured so that leaves are capable of stopping at any position along a movement path to form radiation fields of various shapes. Based on this system, a multi-circle spiral intensity-modulated treatment mode can be achieved, and systemic treatment for the whole body of the patient can be achieved without being limited by a size of the beam collimation.

BRIEF DESCRIPTION OF DRAWINGS

To describe the technical solutions in the embodiments of the present disclosure more clearly, the following briefly introduces the accompanying drawings required for describing the embodiments. Apparently, the accompanying drawings in the following description show merely some embodiments of the present disclosure, and a person of ordinary skill in the art may still derive other drawings from these accompanying drawings without creative efforts.

FIG. 1-2 is a schematic structural diagram of another exemplary radiotherapy system according to an embodiment of the present disclosure;

FIG. 2 is a schematic structural diagram of an exemplary multi-leaf collimator according to an embodiment of the present disclosure, wherein FIG. 2 is a top view of the multi-leaf collimator, and the section of the leaf in FIG. 2 is a section in the direction of thickness T of the leaf;

FIG. 3 is a schematic structural diagram of an exemplary leaf according to an embodiment of the present disclosure, wherein FIG. 3 is a structure of a leaf acquired from a lateral direction of the multi-leaf collimator;

FIG. 11-1 is a schematic diagram of a connection relationship among an exemplary control mechanism and various components according to an embodiment of the present disclosure;

FIG. 11-2 is a schematic diagram of a connection relationship among another exemplary control mechanism and various components according to an embodiment of the present disclosure.

DETAILED DESCRIPTION

For clearer descriptions of the technical solutions and advantages of the present disclosure, embodiments of the present disclosure are described in detail hereinafter with reference to the accompanying drawings.

It should be noted that the isocenter of the radiotherapy system involved in the embodiments of the present disclosure refers to an intersection point between a rotating axis of a collimating body (which is considered the center of a radiation field in some situations) and a rotating axis of a gantry. The collimating body is a whole including a precollimator and a multi-leaf collimator.

The radiation field involved in the embodiments of the present disclosure refers to an irradiation area formed by a radiation beam emitted by a radiation source on a plane being vertical to the radiation beam upon the radiation beam passing through an area defined by the collimating body.

The axial direction of the gantry involved in the embodiments of the present disclosure refers to the axial direction of a central axis of the gantry, and the gantry can rotate around the central axis thereof to drive the treatment head thereon to rotate synchronously.

Figure 1:
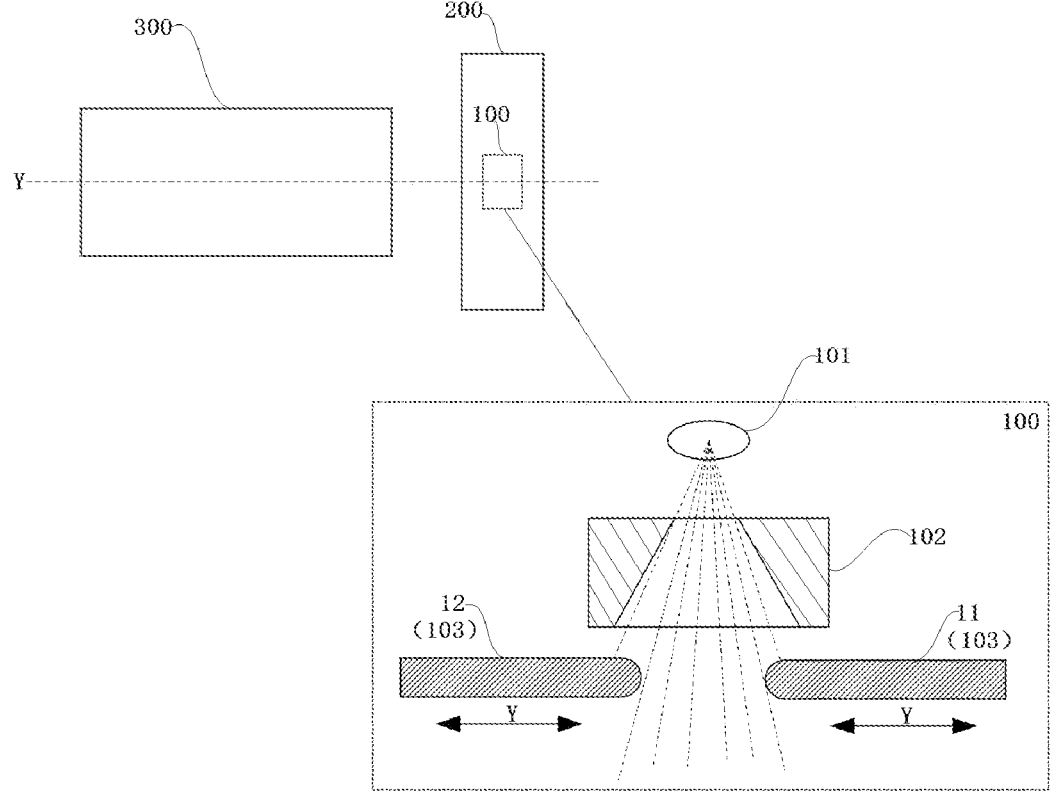
FIG. 1-1 is a schematic structural diagram of an exemplary radiotherapy system according to an embodiment of the present disclosure.
Figures 1, 11:
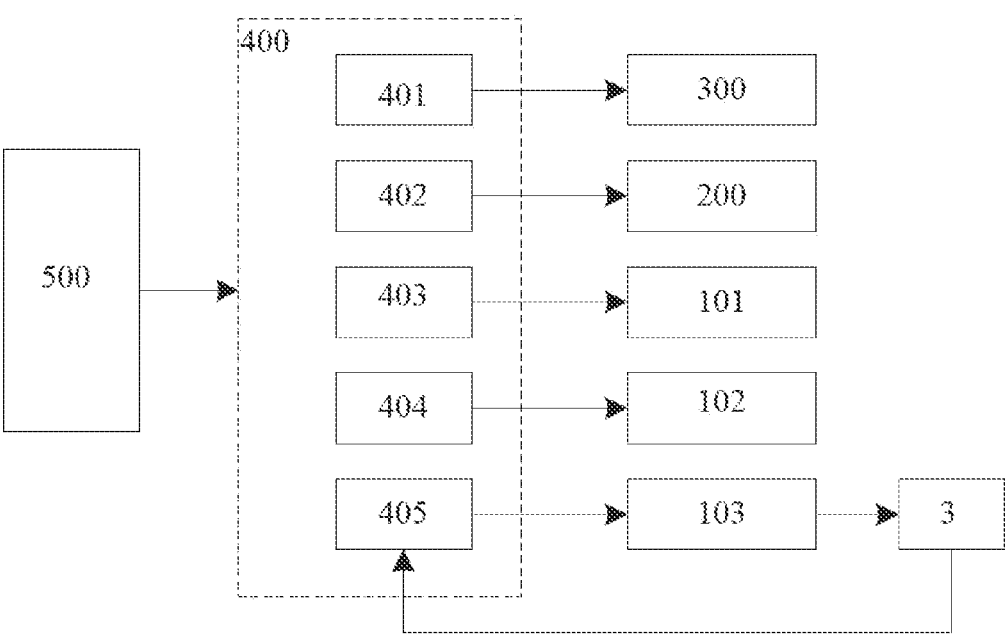
Figures 2, 11:
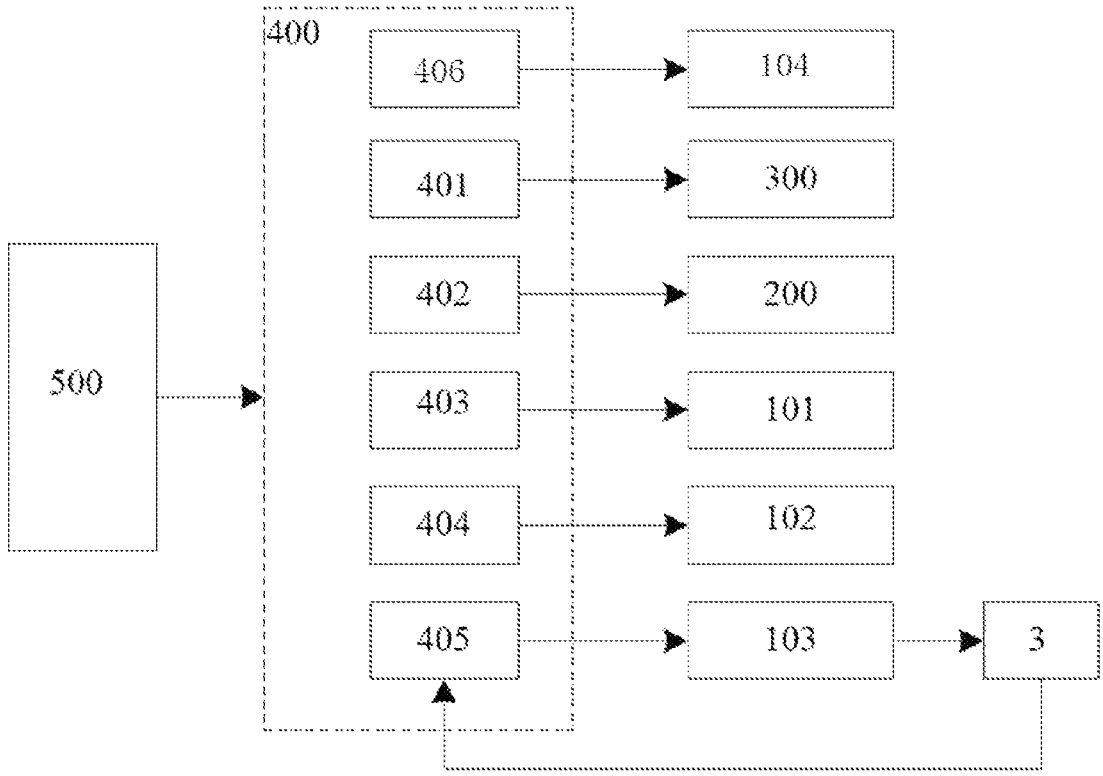

The embodiments of the present disclosure provide a radiotherapy system which, as shown in FIG. 1 and FIG. 11-1, includes a treatment head 100, a gantry 200, a treatment couch 300, and a control mechanism 400; wherein the treatment head 100 is coupled to the gantry 200, and the control mechanism 400 is configured to control the gantry 200 to rotate, and synchronously control the treatment couch 300 to move along an axial direction of the gantry. The treatment head includes a multi-leaf collimator, wherein the multi-leaf collimator is configured so that leaves are capable of stopping at any position along a movement path to form radiation fields of various shapes.

Based on the radiotherapy system according to the embodiments of the present disclosure, during the treatment of the body of the patient, the control mechanism 400 is configured to control the gantry 200 to rotate, and at the same time, control the treatment couch 300 to synchronously move, and the radiation fields of various shapes are formed in cooperation with the multi-leaf collimator, so as to achieve a multi-circle spiral intensity-modulated treatment mode and achieve the effect of spiral treatment. In this way, the treatment range can be enlarged, which is beneficial to the treatment of tumors at any part of the body and of any size, that is, the treatment range is larger, without being limited by the size of the beam collimation. For example, the whole body of the patient, bone marrow of the entire body, or brain and the central nervous system can be treated with systemic therapy at once.

In the radiotherapy system according to some embodiments of the present disclosure, as shown in FIG. 1-1, the treatment head 100 includes a radiation source 101, a precollimator 102, and a multi-leaf collimator 103 with a plurality of groups of leaves; wherein the precollimator 102 and the multi-leaf collimator 103 are sequentially disposed on the path of the radiation beam emitted by the radiation source 101, the precollimator 102 is configured to preliminarily make the radiation beam emitted by the radiation source 101 to conform to a target volume, and the multi-leaf collimator 103 is configured to make the preliminarily changed radiation beam to conform to the target volume again. In some embodiments, the size of a collimating hole of the precollimator in the present disclosure is adjustable.

In some possible embodiments, the control mechanism 400 is configured to control at least two of the treatment couch 300, the gantry 200, the radiation source 101, the precollimator 102, and the multi-leaf collimator 103, so that at least two of the treatment couch 300, the gantry 200, the radiation source 101, the precollimator 102, and the multi-leaf collimator 103 cooperate with each other to improve control accuracy of the radiotherapy system and diversify treatment methods.

In some possible embodiments, as shown in FIG. 11-1, the control mechanism 400 includes a treatment couch controller 401, a gantry controller 402, a radiation source controller 403, a precollimator controller 404, and a multi-leaf collimator controller 405. At least two of the treatment couch controller 401, the gantry controller 402, the radiation source controller 403, the precollimator controller 404, and the multi-leaf collimator controller 405 perform linkage control.

With the synergy of respective controllers, at least two of the treatment couch 300, the gantry 200, the radiation source 101, the precollimator 102, and the multi-leaf collimator 103 cooperate with each other, so as to improve the control accuracy of the radiotherapy system and diversify the treatment methods.

Figures 1, 2:
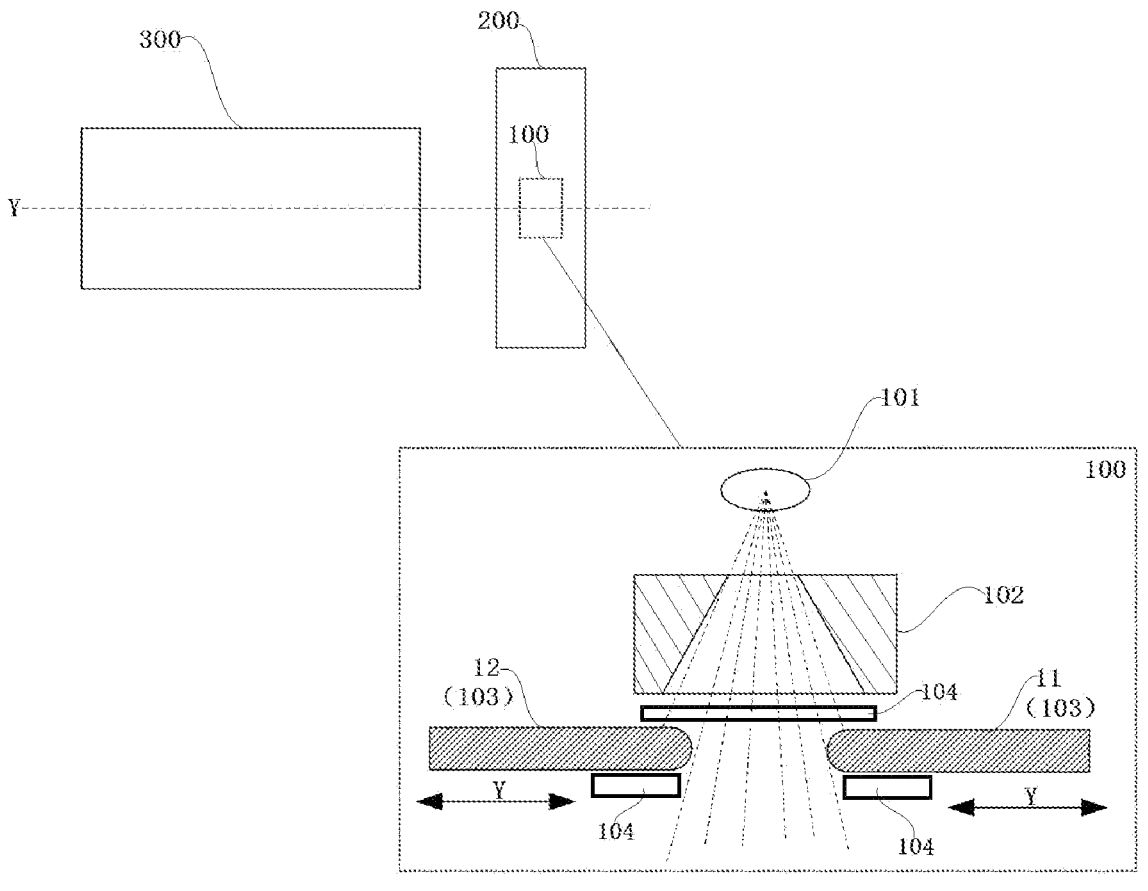
Figure 2:
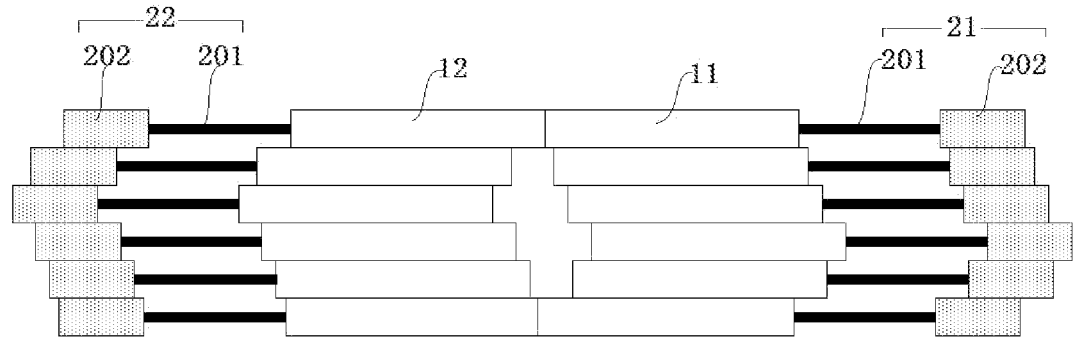

In some possible embodiments, as shown in FIG. 1-2, the treatment head 100 includes the radiation source 101, the precollimator 102 with a pre-collimating hole, the multi-leaf collimator 103 with a plurality of groups of leaves, and a tungsten door 104. The precollimator 102, the multi-leaf collimator 103, and the tungsten door 104 are sequentially disposed on the path of the radiation beam emitted by the radiation source 101. The precollimator 102 is configured to preliminarily change the shape of the radiation beam emitted by the radiation source 101 to conform to a target volume, the multi-leaf collimator 103 is configured to finally change the shape of the preliminarily shape-changed radiation beam to conform to the target volume, and the tungsten door 104 is configured to shield the leaked radiation beam.

The control mechanism 400 is configured to control at least two of the treatment couch 300, the gantry 200, the radiation source 101, the precollimator 102, and the multi-leaf collimator 103, so that at least two of the treatment couch 300, the gantry 200, the radiation source 101, the precollimator 102, the multi-leaf collimator 103, and the tungsten door 104 cooperate with each other, to improve the control accuracy of the radiotherapy system and diversify the treatment methods.

In some embodiments, the control mechanism is configured to enable the gantry, the treatment couch, the multi-leaf collimator, and the radiation source to cooperate, to achieve intensity-modulated irradiation. In some embodiments, the control mechanism is configured to control a rotating speed of the gantry, a speed of the treatment couch, a position of a leaf of the multi-leaf collimator, or a dose rate of the radiation source, so as to modulate the intensity distribution of beam on the target volume. In some embodiments, by controlling the speed of the gantry, the irradiation time of the beam emitted by the radiation source in the radiation field is different, so as to achieve intensity modulation on the target volume. In some embodiments, by controlling the speed of the treatment couch, the irradiation time of the beam emitted by the radiation source in the radiation field is different, so as to achieve intensity modulation on the target volume. In some embodiments, by controlling the position of the leaf of the multi-leaf collimator, the shape of the radiation source is modulated. In some embodiments, part of the target volume is irradiated by making the shape of leaves conform to the target volume, so as to achieve intensity modulation on the target volume. In some embodiments, the radiation dose is controlled to be, for example, 6 MV or 10 MV, so as to achieve intensity modulation on the target volume.

In some embodiments, the control mechanism is configured to control the gantry to rotate, the treatment couch to move along the axial direction of the gantry, and the leaf of the multi-leaf collimator to move during an emission process of the radiation beam by the radiation source. In some embodiments, the radiation source continuously emits the radiation beam, at the same time, the gantry rotates, the treatment couch moves, and the leaves move for conforming to the target volume. The leaf moves to conform to the shapes of the radiation fields under different gantry angles, so that the treatment couch can carry the patient for whole body radiotherapy.

In some embodiments, the control mechanism is configured to control the gantry to rotate to a specific angle, control the treatment couch to move to a specific position along the axial direction of the gantry, control the leaves of the multi-leaf collimator to conform to a specific shape of the radiation field, and control the radiation source to emit the radiation beam. In some embodiments, the gantry and the treatment couch move to a specific position, and the leaves of the multi-leaf collimator form the radiation fields of different shapes through leaf movement at this position. Alternatively, the gantry moves to a specific position, the treatment couch moves, and at the same time, the leaves of the multi-leaf collimator form the radiation fields of different shapes through leaf movement at this position.

In some embodiments, the control mechanism is configured to control a moving speed, a moving direction, and a moving distance of the treatment couch; and/or control a rotating speed, a rotating direction, and a rotating angle of the gantry; and/or control a radiation dose of a radiation beam emitted by the radiation source; and/or control moving speeds and moving distances of the leaves. In some embodiments, the control mechanism respectively controls the treatment couch, the gantry, the radiation source, and the multi-leaf collimator, and meets treatment requirements through cooperation thereof.

As shown in FIG. 11-2, the control mechanism 400 includes the treatment couch controller 401, the gantry controller 402, the radiation source controller 403, the precollimator controller 404, the multi-leaf collimator controller 405, and a tungsten door controller 406. At least two of the treatment couch controller 401, the gantry controller 402, the radiation source controller 403, the precollimator controller 404, the multi-leaf collimator controller 405, and the tungsten door controller 406 perform linkage control.

With the synergy of different controllers, at least two of the treatment couch 300, the gantry 200, the radiation source 101, the precollimator 102, the multi-leaf collimator 103, and the tungsten door 104 cooperate with each other, so that the control accuracy of the radiotherapy system can be improved and the treatment methods can be diversified.

In some embodiments, the treatment couch controller 401, the gantry controller 402, the radiation source controller 403, the precollimator controller 404, the multi-leaf collimator controller 405, and the optional tungsten door controller 406 are integrated to achieve a control mechanism 400 with an integrated structure.

In some embodiments, as shown in FIG. 11-1 or FIG. 11-2, the control mechanism 400 is also connected to an upper computer 500. By operating the upper computer 500, an operator can send an adjustment instruction (that is, a treatment plan) to the control mechanism 400, specifically to the plurality of controllers included in the control mechanism 400, and the controllers in the control mechanism 400 receive the treatment plan and control operation processes of the treatment couch 300, the gantry 200, the radiation source 101, the precollimator 102, and the multi-leaf collimator controller 103 based on the treatment plan.

In some embodiments, as mentioned above, the treatment couch controller 401 and the gantry controller 402 perform linkage control. In this way, during the rotating of the gantry 200, the treatment couch 300 moves synchronously along the axial direction of the gantry 200, thereby achieving spiral treatment.

Further, the multi-leaf collimator controller 405 performs linkage control with the treatment couch controller 401 and the gantry controller 402, so that during the synchronous movement of the treatment couch 300 and the gantry 200, the multi-leaf collimator 103 is opened or closed, therefore the radiotherapy system performs conformal treatment at any position or multiple set positions.

That is, during the rotating process of the gantry 200, the treatment couch 300 moves along the axial direction of the gantry 200 at the same time. At the same time, the multi-leaf collimator 103 also performs synchronous leaf conformal movement to achieve shape conformation and intensity-modulated treatment. Moreover, in the case that the gantry 200 rotates to any position, the multi-leaf collimator 103 performs the leaf conformal movement at the corresponding position, or in the case that the gantry 200 rotates to several specific set positions, the multi-leaf collimator 103 performs the leaf conformal movement at these set positions.

In some embodiments, the control mechanism is configured to receive the treatment plan and control the treatment couch, the gantry, the radiation source, and the multi-leaf collimator based on the treatment plan. In some embodiments, the upper computer receives the treatment plan and sends the treatment plan to each control mechanism.

In some embodiments, the control mechanism is configured to enable the gantry, the treatment couch, the multi-leaf collimator, and the radiation source to cooperate to achieve intensity-modulated irradiation. In some embodiments, the control mechanism is configured to control the rotating speed of the gantry, the speed of the treatment couch, the position of the leaf of the multi-leaf collimator, or the dose rate of the radiation source, so as to modulate the intensity distribution of the radiation field.

In some embodiments, the control mechanism is configured to control the gantry to rotate, the treatment couch to move along the axial direction of the gantry, and the leaves of the multi-leaf collimator to move during the emitting process of the radiation beam by the radiation source. That is, during the irradiation of the radiation source, the gantry and the leaves of the multi-leaf collimator move in cooperation to achieve intensity-modulated irradiation.

Figure 12:
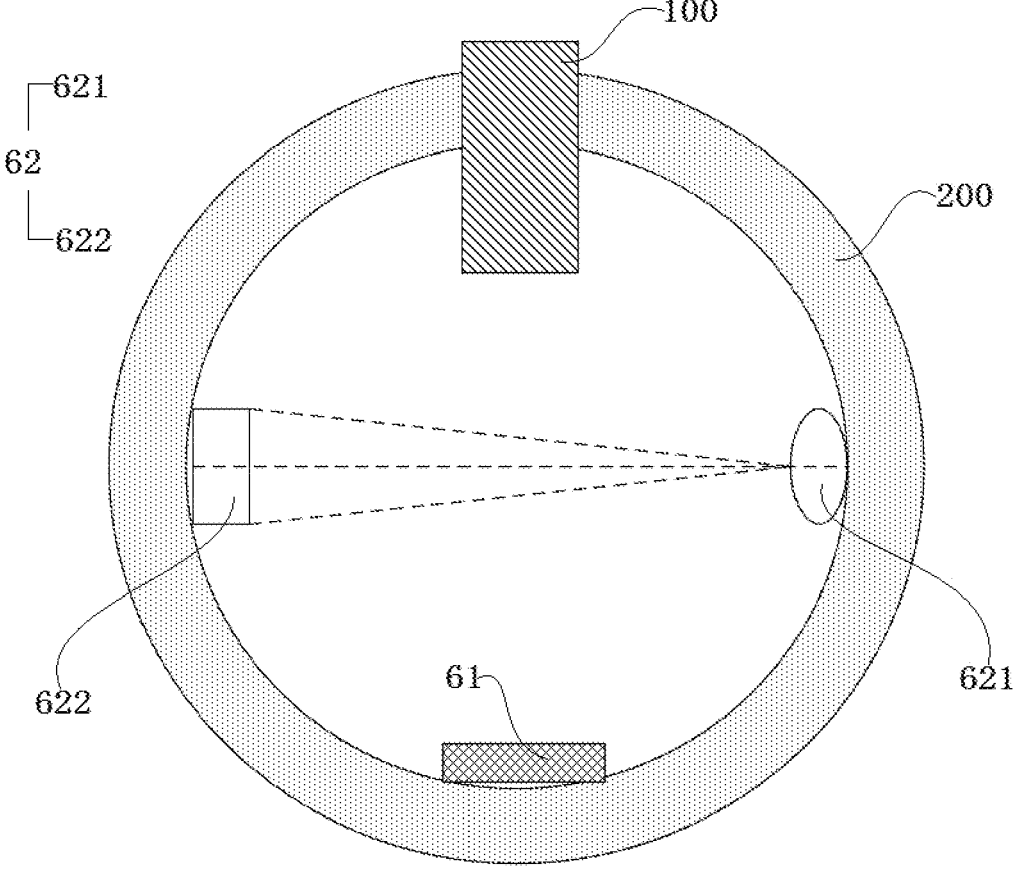
FIG. 12 is a schematic diagram of an arrangement relationship of an exemplary imaging assembly according to an embodiment of the present disclosure.

In some embodiments, the control mechanism is configured to control the gantry to rotate to a specific angle, control the treatment couch to move, along the axial direction of the gantry, to a specific position, control the leaves of the multi-leaf collimator to conform to a specific shape of the radiation field, and control the radiation source to emit the radiation beam. In some embodiments, as shown in FIG. 12, the gantry drives the treatment head to rotate to the 12 o'clock position, the treatment couch moves to the specific position along the axial direction of the gantry, the leaves of the multi-leaf collimator conform to the specific shape of the radiation field, and the radiation source emits the radiation beam.

In some embodiments, during the treatment process along the spiral path formed by the synchronous movement of the treatment couch 300 and the gantry 200, in the case that the gantry 200 rotates to any position, the multi-leaf collimator 103 simultaneously controls the leaves to move on the movement path thereof and stops at any position, to achieve radiation beam shape conformation so as to achieve the purpose of treatment. The way shown in this embodiment can be considered as combining the advantages of the spiral treatment way and VMAT (volumetric modulated arc therapy): during emission of the radiation beam, the gantry rotates, the leaves of the multi-leaf collimator move, in the case that the gantry rotates for a specific angle range, multiple different radiation fields are formed, the irradiation range is larger, and greater flexibility and accuracy are achieved, so that the dose distribution is better, normal tissues are better protected, the dose distribution in the target volume is more uniform, the treatment effect is better, and the side effects of radiotherapy are less. Therefore, the larger treatment range is achieved without being limited by the size of the beam collimation. For example, the whole body of the patient, bone marrow of the entire body, or brain and the central nervous system can be treated with systemic therapy at once.

In some embodiments, during the treatment process along the spiral path formed by the synchronous movement of the treatment couch 300 and the gantry 200, the multi-leaf collimator 103 moves and conforms to the shapes of different radiation fields in the case that the gantry 200 rotates to several fixed set positions, to achieve radiation beam shape conformation at these several set positions so as to achieve the purpose of treatment. The way shown in this embodiment can be considered as combining the advantages of the spiral treatment way and IMRT (intensity-modulated radiotherapy).

In some embodiments, in the case that the treatment head is configured to rotate around the axis thereof, the radiotherapy system according to the embodiments of the present disclosure further includes a treatment head controller, wherein the treatment head controller is configured to control a rotating direction and a rotating angle of the treatment head.

As for the treatment couch controller 401, the treatment couch controller 401 is configured to control the moving speed, moving direction, and moving distance of the treatment couch 300.

The treatment couch 300 is configured to carry the patient and drive the patient to move along the axial direction of the gantry 200. Before the treatment starts, the patient lies on treatment couch 300, and then the patient is driven by the treatment couch 300 to move to the treatment area.

In some embodiments, the treatment couch controller 401 controls the moving speed of the treatment couch 300, so that the treatment couch 300 moves at a uniform speed, or a non-uniform speed, or a uniform speed for a distance, and then a non-uniform speed for another distance during the moving process along the axial direction of the gantry 200.

In some embodiments, the treatment couch controller 401 controls the moving direction of the treatment couch 300, so that the treatment couch 300 moves forward along the axial direction of the gantry 200 (the direction close to the treatment head), backward along the axial direction of the gantry 200 (the direction away from the treatment head), or reciprocates along the axial direction of the gantry 200.

In some embodiments, the treatment couch controller 401 controls the moving distance of the treatment couch 300, so that the treatment couch 300 moves to a specific position. In some embodiments, the treatment couch 300 moves continuously until reaching a target position, or the treatment couch 300 moves several times at intervals according to the treatment requirements, each time moving for a specific distance.

The gantry 200 involved in the embodiments of the present disclosure refers to a rotating gantry. It is understandable that the radiotherapy system also includes a fixed gantry. The fixed gantry is fixedly disposed on the ground, and the rotating gantry is rotatably connected with the fixed gantry. At the same time, the rotating gantry is also fixedly connected with the treatment head, and the rotating gantry drives the treatment head to rotate around the central axis of the rotating gantry. In some embodiments, the structure of the rotating gantry includes, but is not limited to, an annular structure, a C-shaped structure, a helmet-shaped structure, a mechanical arm structure, and the like. In some embodiments, the annular gantry is configured to carry the treatment head, and the annular gantry can rotate and drive the radiation source 101 to rotate together.

As for the gantry controller 402, the gantry controller 402 is configured to control the rotating speed, rotating direction, and rotating angle of the gantry 200.

In some embodiments, the gantry controller 402 is configured to control the rotating speed of the gantry 200, so that the gantry 200 rotates at a uniform speed (in the case of rotating at a uniform speed, the rotating speed of the gantry 200 can be adaptively adjusted according to actual treatment needs) or a non-uniform speed.

In some embodiments, the gantry controller 402 is configured to control the rotating direction of the gantry 200, so that the gantry 200 rotates clockwise or counterclockwise, or switches the rotating direction during rotating, for example, rotates clockwise at first and then counterclockwise, or rotates counterclockwise at first and then clockwise.

In some embodiments, the gantry controller 402 is configured to control the rotating angle of the gantry 200, so that the gantry 200 rotates back and forth within a predetermined angle range, for example, within the range of 0° to 360° or 30° to 90°, or the gantry 200 directly rotates to a specific angle, so that the dose received by the tumors meets the requirements of radiotherapy plan in one treatment area.

In the embodiments of the present disclosure, the radiation source 101 emits the radiation beam, wherein the radiation beam includes α rays, β rays, γ rays, x rays, electron beams, proton beams, and other particle beams generated by radioisotopes. The radiation source controller 403 is configured to control the radiation dose of the radiation beam.

In the embodiments of the present disclosure, two tungsten doors 104 with perpendicular opening and closing directions are disposed, or one tungsten door 104 is disposed. In the case of two tungsten doors 104 being provided, one tungsten door 104 is disposed between the precollimator 102 and the multi-leaf collimator 103, and the other tungsten door 104 is disposed on one side of the multi-leaf collimator 103 away from the radiation source 101. In some embodiments, the two tungsten doors 104 are disposed between the precollimator 102 and the multi-leaf collimator 103 at the same time, or the two tungsten doors 104 are disposed at one side of the multi-leaf collimator 103 away from the radiation source 101 at the same time. The tungsten door controller 406 is configured to control the moving speed and moving distance of the tungsten door 104.

In some embodiments, the precollimator controller 404 is configured to control the size of the pre-collimating hole, so that the size of the pre-collimating hole is adjusted to a desired position to acquire an appropriate radiation field area.

In the embodiments of the present disclosure, the multi-leaf collimator 103 includes a plurality of groups of leaves, and the multi-leaf collimator controller 405 is configured to control the moving speeds and moving distances of the leaves, so that the size, shape, and position of a final collimating hole are adjustable, which is beneficial to intensity-modulated therapy.

In some possible embodiments, as shown in FIG. 2, the multi-leaf collimator 103 includes a plurality of leaf groups disposed along a beam direction, that is, the multi-leaf collimator 103 is a multi-level multi-leaf collimator. Each leaf group includes a first leaf bank 11 and a second leaf bank 12 which are oppositely disposed.

Leaves of both the first leaf bank 11 and the second leaf bank 12 move along a direction parallel to an axis of the gantry 200 of the radiotherapy system (the axial direction of the gantry 200 is the direction of a straight line where the central axis located, the gantry 200 can rotate around the central axis thereof, and the axial direction of the gantry 200 is defined as the Y direction in the embodiments of the present disclosure).

According to the embodiments of the present disclosure, leaves of both the first leaf bank 11 and the second leaf bank 12 move in the direction parallel to the axis of the gantry 200 of the radiotherapy system. In this way, the directions of the conformal movements of leaves of the first leaf bank 11 and the second leaf bank 12 are always parallel to the axial direction of the gantry 200 no matter any position the treatment head 100 rotates to along with the gantry 200, thereby effectively avoiding the influence of gravity during the conformal movements of the leaves, and improving the accuracy of the multi-leaf collimator 103 for radiation beam shape conformation (in the related art, in the case that the multi-leaf collimator rotates to the side part of the gantry (the position reached upon rotating for 90° from an initial position), the multi-leaf collimator is opened and closed in a tangential direction of the gantry, at this time, the directions of the conformal movements of the leaves are along the gravity direction, and the gravity adversely affects the movement of the leaves).

In order to optimize this effect, the treatment head 100 is configured not to rotate around the axis thereof, that is, the treatment head 100 and the gantry 200 always keep a relatively fixed relationship, and the treatment head 100 cannot rotate along the gantry 200 and can only rotate along with the gantry 200.

It should be noted that in the treatment head 100, the radiation source 101, the precollimator 102, and the multi-leaf collimator 103 are all fixedly disposed, so that the precollimator 102 and the multi-leaf collimator 103 are sequentially disposed on the path of the radiation beam emitted by the radiation source 101. Because the treatment head 100 cannot rotate around the axis thereof, the corresponding precollimator 102 and multi-leaf collimator 103 cannot perform corresponding rotation movement.

In some possible embodiments, for the treatment head 100 according to the embodiment of the present disclosure, as shown in FIG. 1-1, the multi-leaf collimator 103 further includes:

a plurality of first drive mechanisms 21 corresponding to the first leaves 11 one to one and a plurality of second drive mechanisms 22 corresponding to the second leaves 12 one to one.

The first drive mechanism 21 is connected to the leaf of the first leaf bank 11 and the control mechanism 400 (specifically, the multi-leaf collimator controller 405) for driving, under control of the control mechanism 400, the leaf of the first leaf bank 11 to move along a direction parallel to the axis of the gantry 200.

The second drive mechanism 22 is connected to the leaf of the second leaf bank 12 and the control mechanism 400 (specifically, the multi-leaf collimator controller 405) for driving, under control of the control mechanism 400, the leaf of the second leaf bank 12 to move along a direction parallel to the axis of the gantry 200.

Through the above arrangement, each leaf in the multi-leaf collimator 103 is independently driven by one drive mechanism. In this way, the specific first leaf bank 11 and/or the second leaf bank 12 are/is driven for shape conformation respectively, which is beneficial to improve the shape conformation accuracy and achieve the purpose of intensity-modulated therapy.

In the case that the radiation field formed by the precollimator 102 becomes smaller, the moving distances of the leaves of the multi-leaf collimator 103 during the conformal movements are correspondingly reduced, so that the maximum moving distances of the leaves of the first leaf bank 11 and the second leaf bank 12 are also reduced compared with the prior art. In the embodiments of the present disclosure, both the maximum moving distances of the leaves of the first leaf bank 11 and the second leaf bank 12 range from 5 cm to 15 cm, for example, 8 cm or 10 cm.

In some embodiments, in the case that the size of the radiation field in the axial direction of the gantry 200 of the radiotherapy system is 8 cm, the maximum moving distances of the leaves of the first leaf bank 11 and the second leaf bank 12 are 8 cm; and in the case that the size of the radiation field in the axial direction of the gantry 200 of the radiotherapy system is 10 cm, the maximum moving distances of the leaves of the first leaf bank 11 and the second leaf bank 12 are 10 cm. Compared with the prior art (the maximum moving distance of the leaf is generally more than 15 cm, and a 40*40 cm radiation field can be formed at the isocenter plus trolley movement), in the embodiments of the present disclosure, the stroke of the leaf is shortened, so that the length of the leaf is shortened.

In the embodiments of the present disclosure, the first drive mechanism 21 is configured to stop, under the control of the multi-leaf collimator controller 405, the leaf of the first leaf bank 11 at any position within a movement range. The second drive mechanism 22 is configured to stop, under the control of the multi-leaf collimator controller 405, the leaf of the second leaf bank 12 at any position within the movement range.

With this arrangement, each leaf can move to any point in the movable range of the leaf, which is beneficial to improve the shape conformation accuracy of the multi-leaf collimator 103.

In some possible embodiments, as shown in FIG. 2, each of the first drive mechanism 21 and the second drive mechanism 22 includes a first transmission member 201 and a first drive member 202; wherein the first transmission member 201 is connected to the rear end of the leaf of the first leaf bank 11 or the second leaf bank 12; and the first drive member 202 is connected to the first transmission member 201.

That is, the rear end of each leaf of the first leaf bank 11 is connected with one first transmission member 201, and the rear end of each leaf of the second leaf bank 12 is connected with one first transmission member 201. The rear end of the leaf refers to the end part opposite to the front end of the leaf, the front ends of the leaves of the first leaf bank 11 and the second leaf bank 12 refer to the opposite end parts of the leaves of the first leaf bank 11 and the second leaf bank 12, and a region for beam shape conformation is formed between the front ends of the leaves of the first leaf bank 11 and the second leaf bank 12.

The movements of the leaves of the first leaf bank 11 and the second leaf bank 12 are controlled by the first drive mechanism 21 and the second drive mechanism 22 respectively, so that the leaves of the first leaf bank 11 and the second leaf bank 12 can be automatically fixed at set positions upon moving to the set positions.

In some embodiments, the transmission mode of the first transmission member 201 is screw transmission or rack-and-pinion transmission, which are exemplarily explained respectively as follows.

(1) In the case that the transmission mode of the first transmission member 201 is screw transmission, as shown in FIG. 2, the first transmission member 201 is a screw rod, and the first drive member 202 is a linear motor (for example, a miniature linear motor). A first end of the screw rod is connected to the tail end of the leaf of the first leaf bank 11 (or the second leaf bank 12), and a second end of the screw rod is connected to the linear motor.

In some embodiments, the linear motor drives the screw rod to make linear reciprocating movement, and then drives the leaf of the first leaf bank 11 (or the second leaf bank 12) to make corresponding linear movement, so as to achieve the purpose of enabling the leaf of the first leaf bank 11 (or the second leaf bank 12) to make linear reciprocating movement along the axial direction of the gantry 200.

In some embodiments, the second end of the screw rod is connected to the linear motor through a rotor with internal threads, and the first end of the screw rod is fixedly connected to the tail end of the leaf of the first leaf bank 11 (or the second leaf bank 12). In this way, a rotary movement of an output shaft of the linear motor is converted into the linear movement of the screw rod along the rotor, and then the leaves of the first leaf bank 11 (or the second leaf bank 12) are driven to move linearly.

In some embodiments, the screw rod directly serves as the output shaft of the linear motor, and at the same time, the screw rod is connected to the tail end of the leaf of the first leaf bank 11 (or the second leaf bank 12) in a threaded way. In this way, the rotation of the screw rod is directly converted into the linear movement of the leaf of the first leaf bank 11 (or the second leaf bank 12).

Based on the above, it can be seen that in the case that the maximum moving distances of the leaves of the first leaf bank 11 and the second leaf bank 12 are reduced relative to the maximum moving distances of the leaves provided by the prior art, the length of the screw rod corresponding to each leaf is correspondingly shortened, which not only is beneficial to reduce production difficulty of the multi-leaf collimator 103, but also can increase the stability of the multi-leaf collimator 103 and reduce a failure rate. In addition, the multi-leaf collimator 103 according to the embodiments of the present disclosure does not need to increase the stroke of the leaves by devices such as a trolley, thereby further reducing the complexity of the radiotherapy system.

(2) In the case that the transmission mode of the first transmission member 201 is rack-and-pinion transmission, the first transmission member 201 includes a pinion and a rack engaged with each other, and the first drive member 202 is a miniature motor. The rack is fixedly connected to the leaf of the first leaf bank 11 (or the second leaf bank 12), and the pinion is coaxially connected to the miniature motor.

In the case that the miniature motor is started, the pinion is driven to rotate, then the rack engaged therewith is driven to move linearly, and then the moving rack drives the leaf of the first leaf bank 11 (or the second leaf bank 12) to move linearly.

Because the driving speed of the motor is variable, the moving speeds and moving positions of the leaves of the first leaf bank 11 (or the second leaf bank 12) is accurately controlled, and then an accurate beam intensity modulation effect can be acquired.

In the embodiments of the present disclosure, the first drive members 202 of the first drive mechanism 21 and the second drive mechanism 22, such as motors, are connected to the control mechanism 400 (the multi-leaf collimator controller 405), and the multi-leaf collimator controller 405 is connected to the upper computer 500. By operating the upper computer 500, the operator sends a leaf moving distance adjustment instruction to the multi-leaf collimator controller 405, and the multi-leaf collimator controller 405 drives the motor to control the leaf movement upon receiving the instruction.

In some possible embodiments, the multi-leaf collimator 103 further includes a first drive member mounting plate, wherein the first drive member mounting plate is provided with a plurality of mounting positions for respectively fixedly connecting with the plurality of first drive members, so that the positions of the plurality of first drive members are fixed.

Further, in some embodiments, the multi-leaf collimator 103 includes a guide rail box for carrying all the leaves, so that the leaves can move stably along the guide rail box during movement.

In some embodiments, in the case that the radiotherapy system including the multi-leaf collimator 103 according to the embodiments of the present disclosure is used for tumor treatment, the operator sends an instruction for adjusting the leaf moving distance through the upper computer 500 before the treatment. Alternatively, the operator sends the instruction for adjusting the leaf moving distance in real time during the process of treatment.

In some embodiments, in the process of treatment, the driving speed of the motor is adjusted in real time to accurately control the moving speeds and moving positions of the leaves of the first leaf bank 11 and the second leaf bank 12, so as to achieve dose intensity modulation during the process of treatment.

In some possible embodiments, the length directions of the leaves of the first leaf bank 11 and the second leaf bank 12 are both parallel to the axial direction of the gantry 200 of the radiotherapy system.

Figure 3:
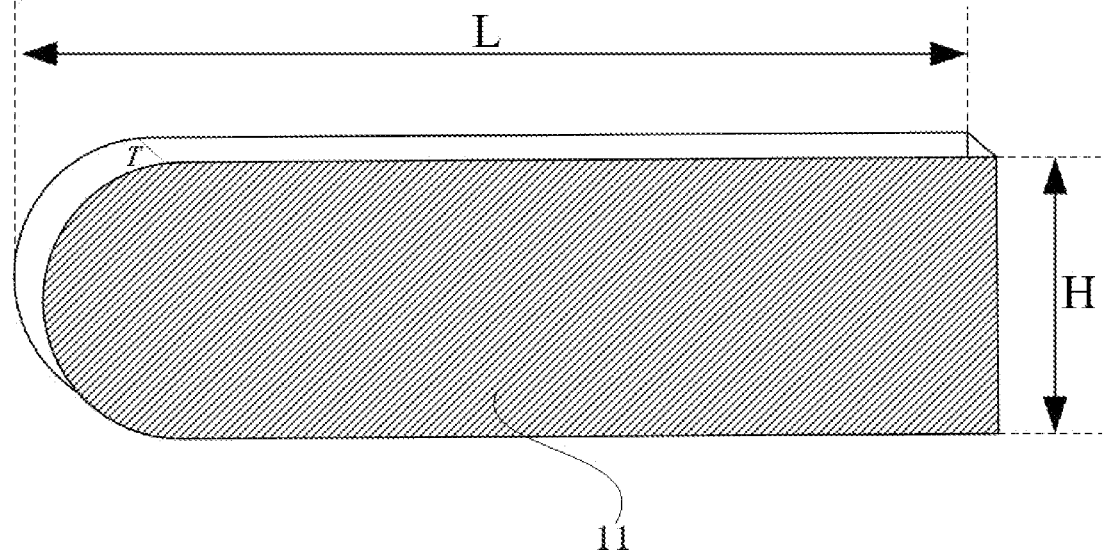

As shown in FIG. 3, both the lengths L of the leaves of the first leaf bank 11 and the second leaf bank 12 range from 2.5 cm to 7.5 cm; and both the heights H of the leaves of the first leaf bank 11 and the second leaf bank 12 range from 6 cm to 8 cm.

The length directions of the leaves of the first leaf bank 11 and the second leaf bank 12 are disposed to be parallel to the axial direction of the gantry 200 of the radiotherapy system (the axial direction of the gantry 200 is defined as the Y direction). In this way, during the conformal movements, the leaves of the first leaf bank 11 and the second leaf bank 12 always move along the axial direction of the gantry 200 of the radiotherapy system, which can prevent the multi-leaf collimator 103 from being influenced by gravity during opening and closing, and improve the accuracy of the multi-leaf collimator 103 for radiation beam shape conformation.

In some possible embodiments, both the lengths L of the leaves of the first leaf bank 11 and the second leaf bank 12 range from 2.5 cm to 7.5 cm, for example, 3 cm, 4 cm, 5 cm, 6 cm, 7 cm, etc. The length L of the leaf refers to the longest size in the length direction, and the above leaf lengths reduce the sizes of the leaves, which finally miniaturizes the leaves of the multi-leaf collimator 103.

In the embodiments of the present disclosure, the leaf length is significantly reduced compared with the leaf length (150 mm) in the prior art, thereby reducing the size and weight of the leaf and reducing manufacturing difficulty and cost. The smaller the weight of the leaf, the lower the friction and movement resistance, the easier the movement to control, and the lower the failure rate. Under the same driving force, the leaf can move faster, thereby significantly improving the treatment quality.

Of course, the leaf size is depending, to some extent, on the size of the radiation field formed by the precollimator 102 at the isocenter, that is, the reduction of the leaf size depends on the reduction of the maximum size of the radiation field formed by the precollimator 102. In some embodiments, in the case that the pre-collimating hole 42 of the precollimator 102 projects a rectangular radiation field at the isocenter of the radiotherapy system, the radiation field includes long sides and short sides. In the case that the length of the short side of the radiation field is 8 cm, both the lengths of the leaves of the first leaf bank 11 and the second leaf bank 12 are set to 4 cm. In the case that the length of the short side of the radiation field is 10 cm, both the lengths of the leaves of the first leaf bank 11 and the second leaf bank 12 are set to 5 cm.

Both the heights H of the leaves of the first leaf bank 11 and the second leaf bank 12 range from 6 cm to 8 cm, for example, 6 cm, 6.5 cm, 7 cm, 7.5 cm, etc. The height direction of the leaf is along an emission direction of the radiation beam. In this height range, not only can the leaf provide a better beam shape conformation effect, but also the leaf is miniaturized.

In the plurality of leaf groups involved in the embodiments of the present disclosure, the thicknesses T of the plurality of first leaves 11 and the plurality of second leaves 12 both gradually decrease from both sides to the middle. That is, in the leaf group, the leaf closer to the middle is thinner, and the leaf closer to both sides is thicker. This arrangement is beneficial to improving the intensity modulation accuracy of the treatment area.

In some possible embodiments, both the opposite front ends of the leaves of the first leaf bank 11 and the second leaf bank 12 are provided with an arc structure, such as a circular arc shape, and further, for example, a semi-circular arc shape. For the first leaf bank 11 and the second leaf bank 12 in the same leaf group, the radians of the front ends of the leaves of the first leaf bank 11 and the second leaf bank 12 are the same or different. In some embodiments, the radians of the front ends of the leaves of the first leaf bank 11 and the second leaf bank 12 are the same.

In the embodiment of the present disclosure, each of the leaves of the first leaf bank 11 and second leaf bank 12 involved includes a rectangular body and an arc-shaped front end disposed at the front end of the rectangular body.

The arc directions of the arc-shaped front ends of the leaves of the first leaf bank 11 and the second leaf bank 12 are both along the height directions of the leaves, and the height direction of the leaf refers to the direction along the emission direction of the radiation beam, that is, the direction perpendicularly passing through the screenshot shown in FIG. 2.

Compared with the front end of the leaf being set as straight and linear, by setting the opposite front ends of the leaves of the first leaf bank 11 and the second leaf bank 12 to be with the arc structure, the multi-leaf collimator 103 according to the embodiments of the present disclosure reduces penumbra formed during the radiation beam passing through the multi-leaf collimator 103, which is beneficial to improve the treatment accuracy.

In order to further optimize the above effect of reducing the penumbra, the radians of the front ends of the leaves of the first leaf bank 11 and the second leaf bank 12 are inversely proportional to the thicknesses of corresponding leaves. That is, the larger the thicknesses T of the leaves, the smaller the radians of the front ends of the leaves; and the smaller the thicknesses T of the leaves, the greater the radians of the front ends of the leaves.

In some embodiments, the radians of the front ends of the leaves of the first leaf bank 11 and the second leaf bank 12 are directly proportional to the distances between the corresponding leaves and the isocenter of the radiotherapy system. That is, the greater the distances between the leaves and the isocenter, the greater the radians of the front ends of the leaves; and the smaller the distances between the leaves and the isocenter, the smaller the radians of the front ends of the leaves.

In some embodiments, the radians of the front ends of the leaves of the first leaf bank 11 and the second leaf bank 12 are directly proportional to the maximum moving distances of the corresponding leaves. That is, the greater the maximum moving distances of the leaves, the greater the radians of the front ends of the leaves; and the smaller the maximum moving distances of the leaves, the smaller the radians of the front ends of the leaves.

Figure 4:
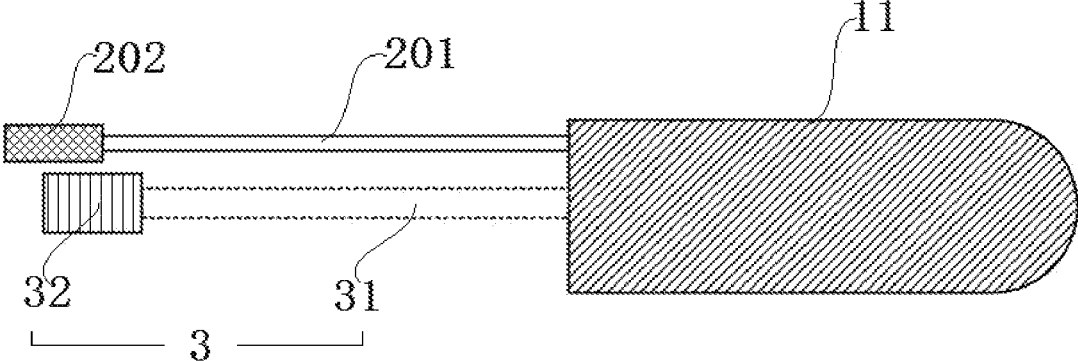
FIG. 4 is a schematic structural diagram of another exemplary multi-leaf collimator.

In some possible embodiments, as shown in FIG. 4, the treatment head 100 according to the embodiments of the present disclosure further includes a position monitoring mechanism 3 configured to monitor the moving positions of the leaves of the first leaf bank 11 and the second leaf bank 12. The position monitoring mechanism 3 is configured to accurately monitor the movement and displacement of the leaves, so as to further improve the shape conformation accuracy of the multi-leaf collimator 103 for the radiation beam and achieve accurate radiotherapy. For each leaf, one position monitoring mechanism 3 is disposed correspondingly. The position monitoring mechanism is not limited in the present disclosure, and may be, for example, a magnetic sensor, a resistance sensor, etc.

In some embodiments, as shown in FIG. 4, the position monitoring mechanism 3 includes a force sensor 32 and an elastic member 31. The force sensor 32 is fixedly disposed, one end of the elastic member 31 is fixedly connected to the force sensor 32, and the other end of the elastic member 31 is connected to the rear end of the leaf of the first leaf bank 11 (the second leaf bank 12).

The force sensor 32 is capable of measuring the force that the elastic member 31 is subjected to. In the case that the leaf of the first leaf bank 11 (the second leaf bank 12) moves, a stretching degree of the elastic member 31 changes, then the force detected by the force sensor 32 changes, and the moving position of the leaf of the first leaf bank 11 (the second leaf bank 12) is determined based on the detected force.

Further, in some embodiments, the position monitoring mechanism 3 includes a processor. The processor is electrically connected to the force sensor 32 and configured to determine the moving position of the leaf of the first leaf bank 11 (the second leaf bank 12) based on the force data measured by the force sensor 32.

In some embodiments, the force sensor 32 is fixed to the drive member mounting plate or on the guide rail box of the multi-leaf collimator 103.

In order to facilitate the measurement, in the case that the elastic member 31 is disposed between the rear end of the leaf of the first leaf bank 11 (the second leaf bank 12) and the force sensor 32, the elastic member 31 is just in a natural elongation state in the case that the leaf is in the initial position. In this way, during the movement of the leaf, only a tensile force that the elastic member 31 is subjected to needs to be measured, and in the case that the leaf returns to the initial position, the theoretical tensile force is zero, which is more convenient for the measurement.

In some embodiments, the elastic member 31 is a spring, and the Hooke coefficient of the spring is fixed within a normal use range, so that the accuracy of the measured data can be ensured. Of course, the elastic member 31 may also include a latex rib, tube, and rope, or a rubber rib, tube or rope, etc., or other parts with good elasticity and fixed Hooke coefficient.

In some embodiments, the position monitoring mechanism 3 is a laser rangefinder. The laser rangefinder includes a spatial wave emitter, a spatial wave receiver, and a processor, wherein the spatial wave emitter emits a spatial wave propagating linearly, and the spatial wave emitted by the spatial wave emitter irradiates the rear end surface of the leaf of the first leaf bank 11 (the second leaf bank 12); the spatial wave receiver is disposed on an optical path of the reflected spatial wave reflected by the rear end surface of the leaf of the first leaf bank 11 (second leaf bank 12) and receives the reflected spatial wave reflected by the rear end surface of the leaf of the first leaf bank 11 (second leaf bank 12); and the processor is connected to the spatial wave emitter and the spatial wave receiver, and determines the position of the corresponding leaf based on the spatial wave emitted by the spatial wave emitter and the spatial wave received by the spatial wave receiver.

In some embodiments, the spatial wave emitter and/or the spatial wave receiver are/is mounted on the drive member mounting plate or the guide rail box of the multi-leaf collimator 103. In some embodiments, the spatial wave is laser, infrared, ultrashort wave, ultrasonic wave, etc.

The processor of the position monitoring mechanism 3 is electrically connected to the multi-leaf collimator controller 405. In this way, the processor can send the moving position information of the first leaf bank 11 (the second leaf bank 12) to the multi-leaf collimator controller 405, so that the multi-leaf collimator controller 405 controls the movement of the leaf of the first leaf bank 11 (the second leaf bank 12) based on the moving position information.

Figure 5:
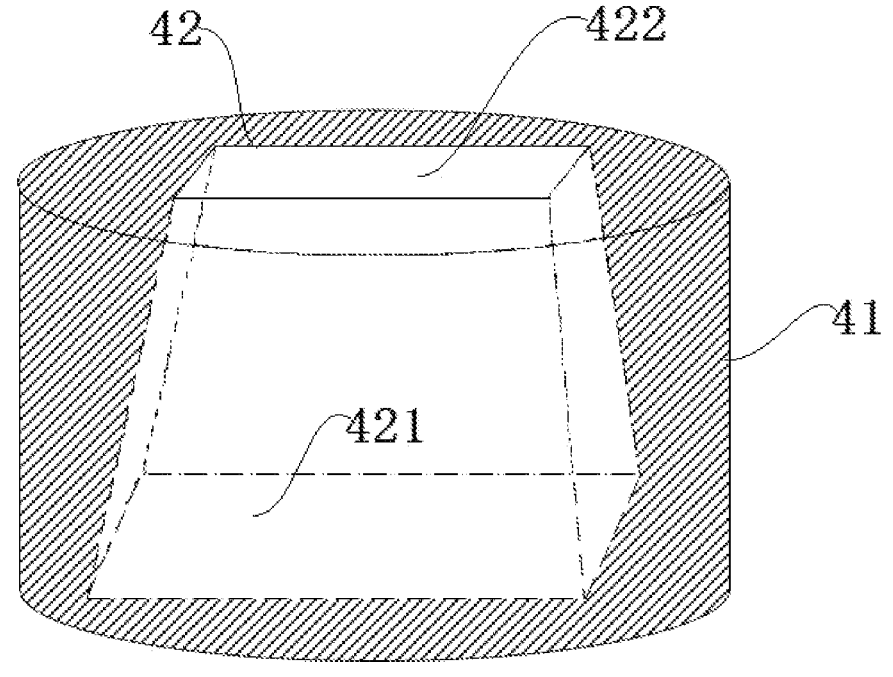
FIG. 5 is a schematic structural diagram of a precollimator according to an embodiment of the present disclosure.
Figure 6:
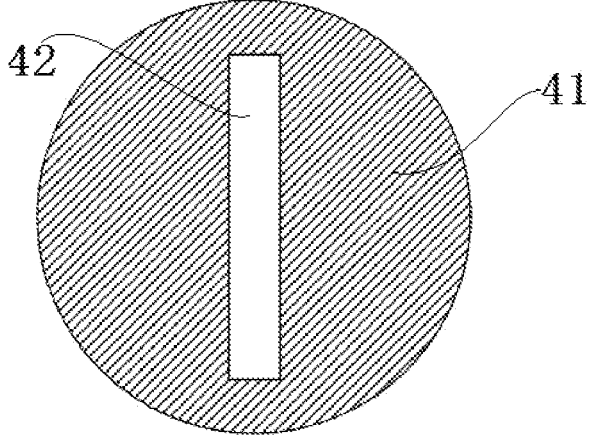
FIG. 6 is a top view of a precollimator according to an embodiment of the present disclosure.
Figure 7:
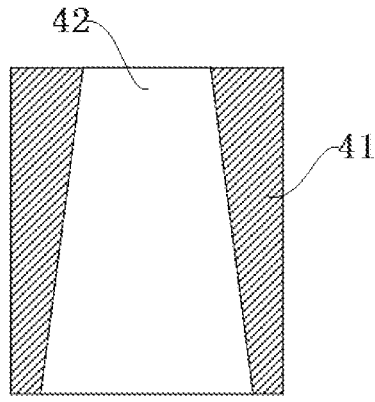
FIG. 7 is a side view of a precollimator according to an embodiment of the present disclosure.

In some possible embodiments, the radiation field projected by the precollimator at the isocenter of the radiotherapy system is non-circular. As shown in FIG. 5 to FIG. 7, the precollimator 102 includes a precollimator body 41 and a pre-collimating hole 42 provided on the precollimator body 41.

The pre-collimating hole 42 is a square truncated pyramid-shaped through hole, and the pre-collimating hole 42 intersects a first surface and a second surface opposite to each other of the precollimator body 41.

The shape of the precollimator body 41 includes, but is not limited to, a circular block, a rectangular block, a pentagonal block, or a block with other geometric shapes, as long as it can be properly installed in the treatment head of the radiotherapy system.

The structure of the square truncated pyramid-shaped through hole is as shown in FIG. 5, which has two groups of inclined inner side surfaces opposite to each other two by two, so that the size of a first cross section of the pre-collimating hole 42 on the first surface of the precollimator body 41 is different from a size of a second cross section of the pre-collimating hole 42 on the second surface of the precollimator body 41.

Inclination angles of the inclined inner side surfaces of the pre-collimating hole 42 is the same or different, as long as the sizes of the first cross section 421 and the second cross section 422 of the pre-collimating hole 42 are different. In some embodiments, the inclination angles of the four inner side surfaces of the pre-collimating hole 42 are the same. In addition, in some embodiments, any cross section of the pre-collimating hole 42 is rectangular or square.

The first surface and the second surface of the precollimator body 41 refer to the surfaces of the precollimator body 41 facing the radiation source and facing the multi-leaf collimator, wherein orientations of the first surface and the second surface are determined based on cross-sectional sizes of the pre-collimating hole 42 at the first surface and the second surface of the precollimator body 41. The surface of one end of the pre-collimating hole 42 that has a smaller cross-sectional size faces the radiation source, and the surface of one end of the pre-collimating hole 42 that has a larger cross-sectional size faces the multi-leaf collimator.

The radiation beam emitted by the radiation source 101 diverges upon passing through the pre-collimating hole 42 with a square truncated pyramid-shaped through hole structure, so that the radiation beam emitted from the pre-collimating hole 42 has a larger radiation field area, which ensures that the radiation beam can completely cover the final collimating hole, and at the same time, it is beneficial to reduce the volume of the precollimator 102.

In some possible embodiments, the first cross section 421 of the pre-collimating hole 42 and the second cross section 422 of the pre-collimating hole 42 are both elongated holes.

The size of the first cross section 421 of the pre-collimating hole 42 is larger than the size of the second cross section 422 of the pre-collimating hole 42.

The first cross section 421 of the pre-collimating hole 42 is a cross section of the pre-collimating hole 42 on the first surface of the precollimator body 41.

The second cross section 422 of the pre-collimating hole 42 is a cross section of the pre-collimating hole 42 on the second surface of the precollimator body 41.

During application, the first surface of the precollimator 102 faces the multi-leaf collimator 103 and the second surface of the precollimator 102 faces the radiation source 101.

In some embodiments, the first cross section and the second cross section of the pre-collimating hole 42 are rectangular or square. Based on the above and FIG. 6, it can be seen that both the first cross section and the second cross section of the pre-collimating hole 42 are elongated holes (rectangular), the elongated holes have long sides and short sides with different lengths, that is, the pre-collimating hole 42 has long sides and short sides. By disposing the structure of the pre-collimating hole 42 as described above, the radiation beam emitted by the radiation source 101 forms a rectangular radiation field at the isocenter position upon passing through the pre-collimating hole 42.

In the case that the precollimator 102 according to the embodiments of the present disclosure is used in the radiotherapy system, the direction of the short sides of the pre-collimating hole 42 is disposed along the axial direction of the gantry 200 of the radiotherapy system.

The shape of the radiation field projected, at the isocenter of the radiotherapy system, by the pre-collimating hole 42 with the cross-sectional shape being an elongated hole is correspondingly a rectangle, including long sides and short sides, wherein the short side direction of the radiation field is along the axial direction of the gantry 200 of the radiotherapy system.

In some possible embodiments, the short side length of the radiation field ranges from 5 cm to 15 cm, such as 5 cm, 6 cm, 7 cm, 8 cm, 9 cm, 10 cm, 11 cm, 12 cm, 13 cm, 14 cm, and 15 cm. The long side length of the radiation field ranges from 30 cm to 50 cm, such as 30 cm, 35 cm, 40 cm, 45 cm, and 50 cm.

In some embodiments, the size of the radiation field projected by the pre-collimating hole 42 at the isocenter of the radiotherapy system is as follows: the short side length of the radiation field is 8 cm or 10 cm, and the long side length of the radiation field is 40 cm.

Based on the size of the radiation field, the size of the pre-collimating hole 42 at any distance from the isocenter is acquired correspondingly, and then the size of the first cross section 421 of the pre-collimating hole 42 and the size of the second cross section 422 of the pre-collimating hole 42 is acquired. Due to the above radiation field size according to the embodiments of the present disclosure, the size of the pre-collimating hole 42 is correspondingly smaller, which is beneficial to reduce the size and volume of the precollimator 102 and further simplify the volume and structure of the treatment head 100.

In some possible embodiments, the size of the pre-collimating hole 42 of the precollimator 102 according to the embodiments of the present disclosure is adjustable, which includes, but is not limited to: the long side size of the pre-collimating hole 42 is adjustable, or the short side size of the pre-collimating hole 42 is adjustable, or both the long side size and the short side size of the pre-collimating hole 42 are adjustable.

By setting the size of the pre-collimating hole 42 being variable, different preliminary radiation beam shape conformation effects can be acquired, and the precollimator 102 is suitable for lesion regions of different sizes, thereby improving the adaptability of the precollimator 102. Further, in the case that the size of the pre-collimating hole 42 changes to zero, that is, in the case that the pre-collimating hole 42 is closed, the source is turned off or intensity modulation treatment without beam irradiation is performed.

In some possible embodiments, the short side size of the pre-collimating hole 42 is adjustable. In this way, under an application state of the precollimator 102, the size of the pre-collimating hole 42 in the axial direction of the gantry 200 of the radiotherapy system is adjustable, so as to adapt to the lesion regions of different sizes.

It should be noted that the short side size of the pre-collimating hole 42 being adjustable means that the short side size of any cross section of the pre-collimating hole 42 is adjustable in the whole depth direction of the pre-collimating hole 42.

For how to adjust the short side size of the pre-collimating hole 42, the embodiments of the present disclosure give the following exemplary description.

Figure 8:
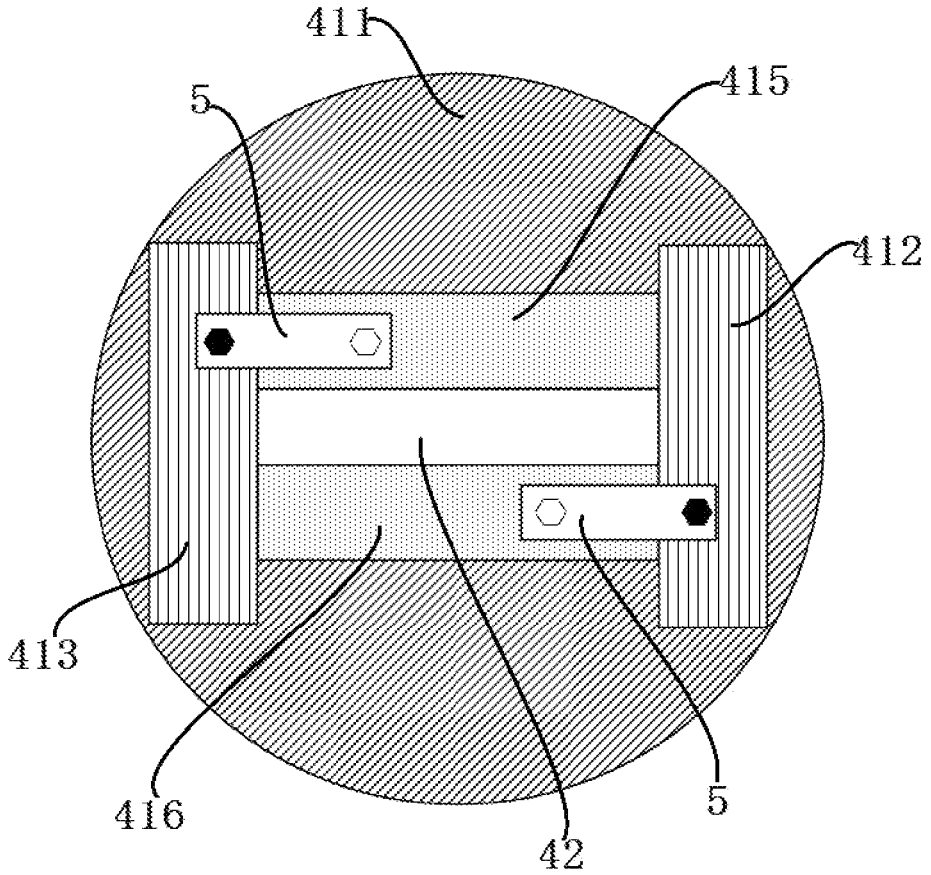
FIG. 8 is a schematic structural diagram of another precollimator according to an embodiment of the present disclosure.
Figure 9:
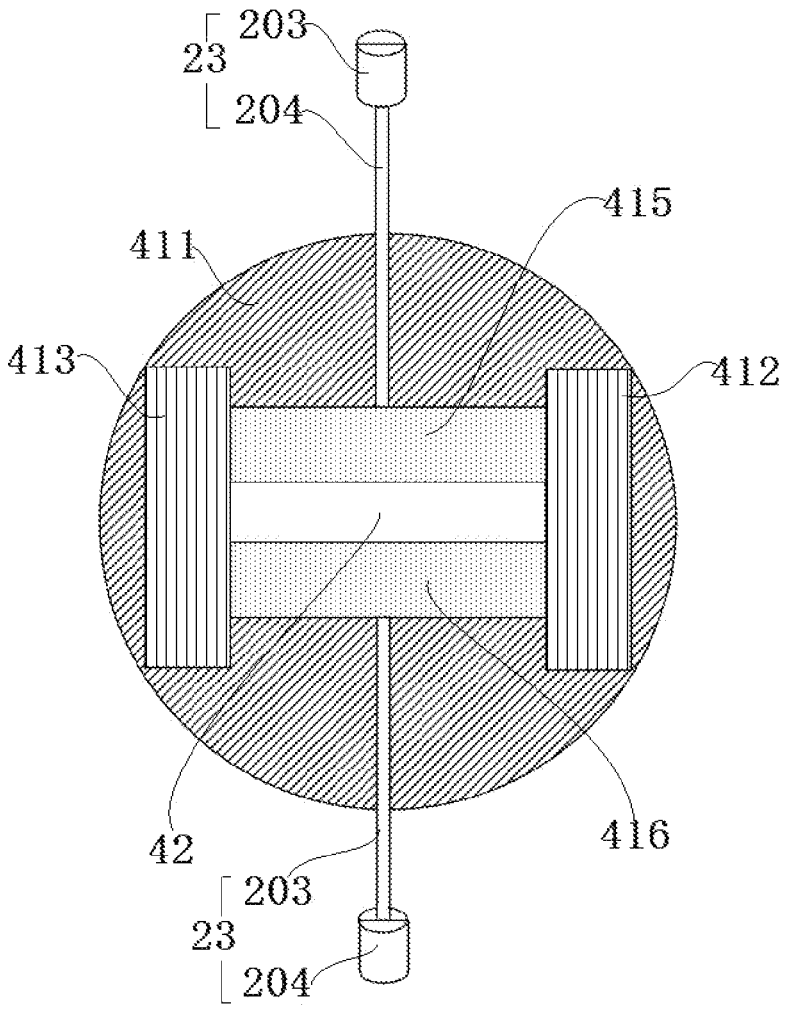
FIG. 9 is a schematic structural diagram of yet another precollimator according to an embodiment of the present disclosure.

In some possible embodiments, as shown in FIG. 8 or FIG. 9, the precollimator body 41 includes a base body 411 with a through hole, a first fixed block 412, a second fixed block 413, a first sliding block 415, and a second sliding block 416.

The first fixed block 412 and the second fixed block 413 are respectively fixed to opposite first side parts of the through hole, to cooperate with each other to form two short sides of the pre-collimating hole 42.

The first sliding block 415 and the second sliding block 416 are respectively disposed at opposite second side parts of the through hole, to cooperate with each other to form two long sides of the pre-collimating hole 42, and the distance between the first sliding block 415 and the second sliding block 416 is adjustable.

Materials of the base body 411, the first fixed block 412, the second fixed block 413, the first sliding block 415, and the second sliding block 416 are all selected from a ray shielding material, such as tungsten, plumbum, or tungsten alloy. Moreover, the shape of the base body 411 includes, but is not limited to, a circular block, a rectangular block, a pentagonal block, or a block with other geometric shapes, as long as it can be properly installed in the treatment head 100 of the radiotherapy system.

By making the first sliding block 415 and the second sliding block 416 move, the distance between the first sliding block 415 and the second sliding block 416 can be adjusted, thereby achieving the purpose of adjusting the size of the short sides of the pre-collimating hole 42.

In some embodiments, the first sliding block 415 and the second sliding block 416 move in the following ways, so as to achieve the purpose of adjusting the distance therebetween: the first sliding block 415 and the second sliding block 416 move by means of sliding guide rail transmission, the first sliding block 415 and the second sliding block 416 move by means of rack-and-pinion transmission, and the first sliding block 415 and the second sliding block 416 move by means of screw rod-and-nut transmission. The following schematically explains these ways.

In some embodiments, the first fixed block 412 and the second fixed block 413 are respectively disposed at two top sides of the through hole of the base body 411, and the first sliding block 415 and the second sliding block 416 are respectively disposed at two top sides of the through hole of the base body 411. In this way, the pre-collimating hole 42 defined by fixed blocks and sliding blocks is located above the through hole of the base body 411. In this implementation, the size of the through hole is greater than the maximum size that the pre-collimating hole 42 can be adjusted to be with, to ensure the desired radiation field.

In some embodiments, the first fixed block 412 and the second fixed block 413 are respectively disposed at two inner sides of the through hole of the base body 411, and the first sliding block 415 and the second sliding block 416 are respectively disposed at two inner sides of the through hole of the base body 411. In this way, the pre-collimating hole 42 defined by fixed blocks and sliding blocks and the through hole of the base body 411 are as a whole.

In the embodiments, it is only necessary to adaptively determine the size of the through hole based on the sizes of the fixed blocks and the sliding blocks and the required radiation field size.

Figure 10:
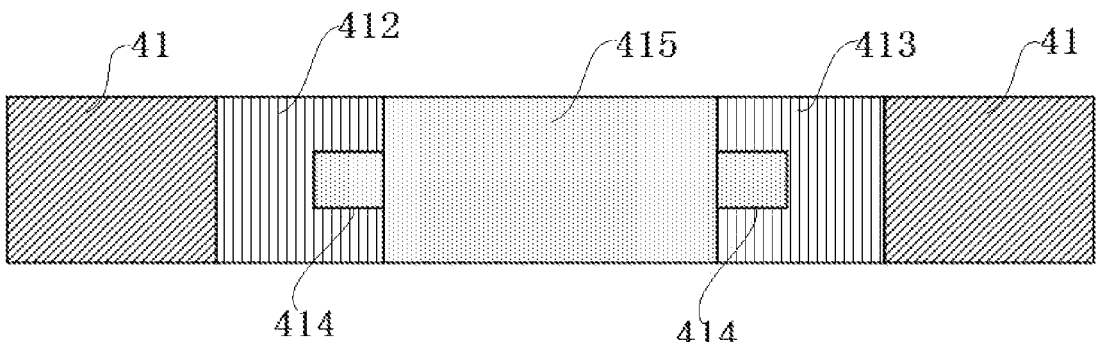
FIG. 10 is a schematic diagram of a connection relationship between a fixed block and a sliding block according to an embodiment of the present disclosure.

The opposite second side parts of the through hole of the base body 411 are provided with chutes (the chutes are equivalent to the following guide grooves 414) to respectively accommodate tails of the first sliding block 415 and the second sliding block 416, and to enable the tails of the first sliding block 415 and the second sliding block 416 to move along the chutes, and front parts of the first sliding block 415 and the second sliding block 416 are opposite to each other, so as to define a radiation beam shape conformation area. The structures of the opposite side parts of the first fixed block 412 and the second fixed block 413 are matched with the structures of the side parts of the first sliding block 415 and the second sliding block 416. In some embodiments, the opposite side parts of the first fixed block 412 and the second fixed block 413 and the side part of the first sliding block 415 are in adaptive surface-to-surface contact, so that the first sliding block 415 and the second sliding block 416 move along the side part surfaces of the fixed blocks. Alternatively, in order to enable the movement of the first sliding block 415 and the second sliding block 416 to be more stable and smooth, as shown in FIG. 10, the opposite surfaces of the first fixed block 412 and the second fixed block 413 are both provided with the guide grooves 414, so that two opposite sides of the first sliding block 415 and two opposite sides of the second sliding block 416 are respectively embedded into the corresponding guide grooves 414, and both the first sliding block 415 and the second sliding block 416 move along the guide grooves 414.

In some embodiments, one of the first sliding block 415 and the second sliding block 416 is fixed and the other moves. In some embodiments, the second sliding block 416 is fixed and the first sliding block 415 moves along a direction away from or close to the second sliding block 416. Alternatively, both the first sliding block 415 and the second sliding block 416 move towards or away from each other.

In some embodiments, the cross-sectional shape of the guide groove 414 includes, but is not limited to, rectangle, trapezoid, arc, etc. Correspondingly, the two opposite sides of the first sliding block 415 and the second sliding block 416 are also set to be rectangle, trapezoid, arc, etc.

The guide grooves 414 in the fixed blocks can not only provide a guide function for the movement of the sliding blocks, but also provide a certain position limiting function for the sliding blocks, which is beneficial to improve the moving stability of the sliding blocks.

In the case that the first sliding block 415 and the second sliding block 416 move, along the guide grooves 414, to set positions, it is necessary to fix the first sliding block 415 and the second sliding block 416. The ways of fixing the sliding blocks include but are not limited to, the following.

In some possible embodiments, the sliding blocks are manually fixed. In this implementation, as shown in FIG. 8, the precollimator 102 according to the embodiments of the present disclosure further includes a fixing member 5 configured to fix the first sliding block 415 and the second sliding block 416 in a moving state.

In the case that the first sliding block 415 and the second sliding block 416 move to the set positions, the first sliding block 415 and the second sliding block 416 are fixed by the fixing member 5, so that the first sliding block 415 and the second sliding block 416 are fixed at the set positions. In the following, the structure of the fixing member 5 is schematically explained by taking that the first sliding block 415 is fixed by the fixing member 5 as an example (the fixing principle of the second sliding block 416 by the fixing member 5 is the same as the fixing principle of the first sliding block 415, and the details are not repeated here).

In some embodiments, the fixing member 5 includes a pressing plate and a first fixing bolt, wherein one end of the pressing plate is rotatably connected to the top of the first fixed block 412 and/or the second fixed block 413, the other end of the pressing plate is provided with a first bolt hole, and the top wall of the first sliding block 415 is provided with a first bolt groove, wherein the first bolt groove is elongated and the length of the first bolt groove extends along a moving direction of the first sliding block 415. The first bolt groove is communicated with the first bolt hole.

In the case that the first sliding block 415 moves to the set position, the first fixing bolt passes through the first bolt hole and enters a first position of the first bolt groove, and is connected to the first bolt hole by threads at the same time, so that the pressing plate presses the first sliding block 415, and the first sliding block 415 is pressed against the top of the base body 411, so as to achieve the purpose of fixing the first sliding block 415. In the case that it is necessary to adjust the position of the first sliding block 415, the first fixing bolt is disassembled, and the pressing plate is rotated to stop pressing the first sliding block 415. In the case that the first sliding block 415 moves to the desired position, the pressing plate is rotated reversely to enable the first bolt hole therein to be communicated with a second position of the first bolt groove in the first sliding block 415, so that the first fixing bolt can pass through the first bolt hole and enter the second position of the first bolt groove, and be connected to the first bolt hole by threads at the same time, so as to achieve the purpose of pressing the first sliding block 415.

In some embodiments, the fixing member 5 includes a second fixing bolt. The side wall of the first sliding block 415 is provided with a plurality of second bolt grooves disposed side by side, wherein the plurality of second bolt grooves are disposed in sequence along the moving direction of the first sliding block 415. The side wall of the first fixed block 412 or the second fixed block 413 is provided with a second bolt hole, wherein the second bolt hole is elongated and the length of the second bolt hole extends along the moving direction of the first sliding block 415. The second bolt hole is communicated with the second bolt grooves, and both the second bolt hole and the second bolt groove can be connected to the second fixing bolt by threads at the same time.

In some embodiments, in the case that the first sliding block 415 moves to the set position, the second fixing bolt passes through the second bolt hole and enters the second bolt grooves, and is connected to both the second bolt hole and the second bolt groove by threads at the same time, so as to achieve the purpose of fixing the first sliding block 415.

In some possible embodiments, as shown in FIG. 9, both the first sliding block 415 and the second sliding block 416 are driven by a third drive mechanism 23 to move. The third drive mechanism 23 includes a second transmission member 203 respectively connected to the first sliding block 415 and the second sliding block 416; and a second drive member 204 connected to the second transmission member 203.

Each of the first sliding block 415 and the second sliding block 416 corresponds to a third drive mechanism 23, and the first sliding block 415 and the second sliding block 416 are individually controlled by two third drive mechanisms 23 respectively. In the embodiments of the present disclosure, the movement processes of the first sliding block 415 and the second sliding block 416 are automatically controlled by using the third drive mechanisms 23, so that the first sliding block 415 and the second sliding block 416 can be automatically fixed at the set positions upon moving to the set positions.

In some embodiments, the transmission mode of the second transmission member 203 is screw transmission or rack-and-pinion transmission, which is schematically explained respectively as follows.

(1) As shown in FIG. 9, in the case that the transmission mode of the second transmission member 203 is screw transmission, the second transmission member 203 is a screw rod, and the second drive member 204 is a linear motor (miniature linear motor). A first end of the screw rod is connected to the tail end of the first sliding block 415 (the tail end of the first sliding block 415 is the end part of the first sliding block 415 away from the second sliding block 416), and a second end of the screw rod is connected to the linear motor.

The linear motor drives the screw rod to make a linear reciprocating movement, and then the first sliding block 415 is driven to make a corresponding linear movement, so as to achieve the purpose of enabling the first sliding block 415 to make a linear reciprocating movement in an extension direction of the central axis of the gantry 200.

In some embodiments, the second end of the screw rod is connected to the linear motor through a rotor with internal threads, and the first end of the screw rod is fixedly connected to the tail end of the first sliding block 415. In this way, the rotary movement of an output shaft of the linear motor is converted into the linear movement of the screw rod along the rotor, and then the first sliding block 415 is driven to move linearly.

Alternatively, the screw rod is directly used as the output shaft of the linear motor, and at the same time, the screw rod is connected to the tail end of the first sliding block 415 by threads. In this way, the rotation of the screw rod is directly converted into the linear movement of the first sliding block 415.

(2) In the case that the transmission mode of the second transmission member 203 is rack-and-pinion transmission, the second transmission member 203 includes a pinion and a rack engaged with each other, and the second drive member 204 is a miniature motor. The rack is fixedly connected to the first sliding block 415, and the pinion is coaxially connected to the miniature motor.

In the case of being started, the miniature motor drives the pinion to rotate, and then drives the rack engaged therewith to move linearly, and the moving rack further drives the first sliding block 415 to move linearly.

Because the driving speed of the motor is variable, the moving speeds and moving positions of the first sliding block 415 and the second sliding block 416 are accurately controlled, and then an accurate ray intensity modulation effect can be acquired.

In the embodiments of the present disclosure, the motor of the third drive mechanism 23 is connected to the precollimator controller 404, and the precollimator controller 404 is also connected to the upper computer 500. By operating the upper computer 500, the operator sends an instruction for adjusting the short side length of the pre-collimating hole 42 to the precollimator controller 404, and the precollimator controller 404 drives the motors to control the sliding blocks to move upon receiving the instruction, thereby achieving the purpose of acquiring the pre-collimating hole 42 of a specific size.

In the case that the radiotherapy system including the precollimator 102 according to the embodiments of the present disclosure is used for tumor treatment, the operator sends an instruction for adjusting the size of the pre-collimating hole 42 through the upper computer 500 before the treatment, to adjust a width of the pre-collimating hole 42 to a set width value. Alternatively, the operator sends an instruction for adjusting the size of the pre-collimating hole 42 in real time during the treatment.

In some embodiments, during the treatment, the driving speed of the motor is adjusted in real time to accurately control the moving speeds and moving positions of the first sliding block 415 and the second sliding block 416.

It should be noted that, based on the above structural arrangement of the multi-leaf collimator 103 and the pre-collimator 102, the radiotherapy system according to the embodiments of the present disclosure is not necessary to be provided with the tungsten door, which is beneficial to simplify the structure of the radiotherapy system, increase the reliability of the radiotherapy system and reduce the cost of the radiotherapy system.

In some possible embodiments, as shown in FIG. 12, the radiotherapy system according to the embodiments of the present disclosure further includes a first imaging assembly 61. The first imaging assembly 61 is disposed oppositely to the treatment head 100, and is configured to acquire first image data based on the radiation beam from the treatment head 100, wherein the first image data is configured for radiation field imaging or dose verification.

In some embodiments, the first imaging assembly 61 is disposed on the gantry 200, and is an EPID (electronic portal imaging device).

In some embodiments, radiation field imaging means acquiring an image based on the radiation beam during the treatment, so as to determine whether the radiation field during the actual treatment is consistent with the radiation field in the treatment plan. In some embodiments, the radiation field imaging means acquiring a medical image of the body of the patient before the treatment, and performing image registration based on the medical image and other medical images of the body of the patient (such as CT images, MR images, or PET images), so as to guide patient positioning. In some embodiments, the radiation field imaging means acquiring a medical image of the body of the patient during the treatment, and performing the image registration based on the medical image and other medical images of the body of the patient (such as the CT images, the MR images, or the PET images), so as to confirm whether the tumor of the body of the patient has moved during the treatment, and then guide the radiotherapy system to implement moveable and accurate treatment for tumor by adjusting the treatment couch or the treatment head. In some embodiments, the treatment couch is moved to enable the tumor to be disposed in an irradiation area, the treatment head is adjusted to turn off the radiation beam or reduce the dose rate, or the radiation beam is blocked by the precollimator or the multi-leaf collimator to prevent normal tissues or organs from being irradiated by the radiation beam.

In some embodiments, dose verification means acquiring image data based on the radiation beam during the treatment, acquiring dose parameters based on the image data, and then determining whether the actual treatment dose is consistent with the dose in the treatment plan.

In some embodiments, in the case that the maximum treatment field of the radiotherapy system according to the embodiments of the present disclosure is 8 cm*40 cm or 10 cm*40 cm, the EPID is an elongated detector with a corresponding size (the size of the EPID is calculated by a geometric relationship based on the size of the maximum radiation field or the size of the pre-collimating hole on the precollimator, and the size of the detector is reduced correspondingly because the size of the pre-collimating hole is significantly reduced compared with the size of the pre-collimating hole in the prior art). Therefore, the size of the detector is reduced, the device space is reduced and the cost of the detector is reduced.

In some possible embodiments, as shown in FIG. 12, the radiotherapy system according to the embodiments of the present disclosure further includes a second imaging assembly 62. The second imaging assembly 62 includes a bulb tube 621 and a flat panel detector 622 which are oppositely disposed. The bulb tube 621 is configured to emit X-rays, and the flat panel detector 622 is configured to detect the X-rays and generate second image data, wherein the second image data is configured for imaging the tumor of the patient.

In some embodiments, the second imaging assembly 62 is disposed on the gantry 200, and the bulb tube 621 is an X-ray source for emitting KV-level rays. During application, the gantry rotates to drive the bulb tube 621 to rotate, during the rotation, the bulb tube 621 generates an X-ray beam, the X-ray beam passes through the human body from different angles and is received by the flat panel detector 622, and the flat panel detector 622 generates a CT image based on the received ray data, thereby achieving tumor imaging of the patient. In some embodiments, the X-ray beam is a fan beam or a cone beam.

In the embodiments of the present disclosure, the terms "first" and "second" are only for descriptive purposes and cannot be understood as indicating or implying relative importance. The term "a plurality of" refers to two or more, unless otherwise explicitly defined.

Described above are merely for the ease of understanding the technical solutions of the present disclosure by those skilled in the art, but are not intended to limit the present disclosure. Any modifications, equivalent replacements, improvements, and the like made within the concept and principles of the present disclosure should be included within the scope of protection of the present disclosure.

What is claimed is:

1. A radiotherapy system, comprising: a treatment couch, a gantry, a treatment head coupled to the gantry, and a control mechanism; wherein the control mechanism is configured to control the gantry to rotate, and synchronously control the treatment couch to move along an axial direction of the gantry; and the treatment head comprises a radiation source, a pre-collimator, and a multi-leaf collimator, the multi-leaf collimator being configured so that leaves are capable of stopping at any position along a movement path to form radiation fields of various shapes, wherein the multi-leaf collimator comprises a first leaf bank and a second leaf bank which are oppositely disposed, leaves of both leaf banks being moveable along a direction parallel to an axis of the gantry.

2. The radiotherapy system according to claim 1, wherein the multi-leaf collimator comprises: a plurality of leaf groups disposed along a beam direction, wherein at least one leaf group comprises the first leaf bank and the second leaf bank which are oppositely disposed.

3. The radiotherapy system according to claim 1, wherein maximum moving distances of the leaves of the first leaf bank and the second leaf bank range from 5 cm to 15 cm.

4. The radiotherapy system according to claim 1, wherein length directions of the leaves of the first leaf bank and the second leaf bank are parallel to the axial direction of the gantry;

lengths of the leaves of the first leaf bank and the second leaf bank range from 2.5 cm to 7.5 cm; and heights of the leaves of the first leaf bank and the second leaf bank range from 6 cm to 8 cm.

5. The radiotherapy system according to claim 1, wherein opposite front ends of the leaves of the first leaf bank and the second leaf bank are both provided with an arc structure;

radians of the front ends of the leaves of the first leaf bank and the second leaf bank are inversely proportional to thicknesses of corresponding leaves; or, radians of the front ends of the leaves of the first leaf bank and the second leaf bank are directly proportional to distances between the corresponding leaves and an isocenter of the radiotherapy system; or, radians of the front ends of the leaves of the first leaf bank and the second leaf bank are directly proportional to maximum moving distances of the corresponding leaves.

6. The radiotherapy system according to claim 1, wherein a radiation field projected by the precollimator at an isocenter of the radiotherapy system is non-circular.

7. The radiotherapy system according to claim 6, wherein the precollimator comprises a precollimator body and a pre-collimating hole provided on the precollimator body; wherein the pre-collimating hole is a square truncated pyramid-shaped through hole, and the pre-collimating hole intersects a first surface and a second surface opposite to each other of the precollimator body.

8. The radiotherapy system according to claim 1, wherein a shape of a radiation field projected by the precollimator at an isocenter of the radiotherapy system is elongated, wherein a direction of a short side of the radiation field is along the axial direction of the gantry of the radiotherapy system.

9. The radiotherapy system according to claim 8, wherein a length of the short side of the radiation field ranges from 5 cm to 15 cm; and/or, a length of a long side of the radiation field ranges from 30 cm to 50 cm.

10. The radiotherapy system according to claim 7, wherein a size of a short side of the pre-collimating hole is adjustable.

11. The radiotherapy system according to claim 1, wherein the control mechanism is configured to receive a treatment plan and, based on the treatment plan, control the treatment couch, the gantry, the radiation source, and the multi-leaf collimator.

12. The radiotherapy system according to claim 1, wherein the treatment head further comprises: a tungsten door; and the control mechanism is configured to control at least two of the treatment couch, the gantry, the radiation source, the precollimator, the multi-leaf collimator, and the tungsten door.

13. The radiotherapy system according to claim 1, wherein the control mechanism is configured to enable the gantry, the treatment couch, the multi-leaf collimator, and the radiation source to cooperate to achieve intensity-modulated irradiation.

14. The radiotherapy system according to claim 13, wherein the control mechanism is configured to control a rotating speed of the gantry, a speed of the treatment couch, a position of a leaf in the multi-leaf collimator, or a dose rate of the radiation source, so as to perform intensity modulation on a target volume.

15. The radiotherapy system according to claim 1, wherein the control mechanism is configured to control the gantry to rotate, the treatment couch to move along the axial direction of the gantry, and the leaf of the multi-leaf collimator to move during an emitting process of a radiation beam by the radiation source.

16. The radiotherapy system according to claim 1, wherein the control mechanism is configured to control the gantry to rotate to a specific angle, control the treatment couch to move, along the axial direction of the gantry, to a specific position, control the leaves of the multi-leaf collimator to conform to a radiation field with a specific shape, and control the radiation source to emit a radiation beam.

17. The radiotherapy system according to claim 13, wherein the control mechanism is configured to
  control a moving speed, a moving direction, and a moving distance of the treatment couch; and/or
  control a rotating speed, a rotating direction, and a rotating angle of the gantry; and/or
  control a radiation dose of the radiation beam emitted by the radiation source; and/or control moving speeds and moving distances of the leaves of the first leaf bank and/or the second leaf bank.

18. The radiotherapy system according to claim 1, wherein the radiotherapy system further comprises a first imaging assembly disposed oppositely to the treatment head and configured to acquire first image data based on a radiation beam from the treatment head, the first image data being configured for radiation field imaging or dose verification.

19. The radiotherapy system according to claim 1, wherein the radiotherapy system further comprises a second imaging assembly, wherein the second imaging assembly comprises a bulb tube and a flat panel detector that are oppositely disposed, the bulb tube being configured to emit X-rays, and the flat panel detector being configured to detect the X-rays and generate second image data, the second image data being configured to image a tumor of a patient.

* * * * *